United States Patent [19]

Reiffenrath et al.

[11] Patent Number: 6,126,857
[45] Date of Patent: Oct. 3, 2000

[54] BISALKENYLBICYCLOHEXANES, AND LIQUID-CRYSTALLINE MEDIUM

[75] Inventors: Volker Reiffenrath, Rossdorf; Harald Hirschmann, Darmstadt, both of Germany

[73] Assignee: Merck Patent Gesellschaft mit Beschrankter Haftung, Germany

[21] Appl. No.: 08/942,548

[22] Filed: Oct. 1, 1997

[30] Foreign Application Priority Data

Oct. 2, 1996 [DE] Germany .......................... 196 40 851
Feb. 27, 1997 [DE] Germany .......................... 197 07 950

[51] Int. Cl.$^7$ .......................... C09K 19/30; C07C 13/18
[52] U.S. Cl. .................. 252/299.63; 568/664; 585/20
[58] Field of Search ................ 252/299.63; 568/664; 585/20, 350

[56] References Cited

U.S. PATENT DOCUMENTS 5,238,602  8/1993  Petrzilka et al. ............ 252/299.65
5,776,367  7/1998  Matsui et al. ............... 252/299.63

FOREIGN PATENT DOCUMENTS 427957   1/1995   European Pat. Off. .
471287   6/1995   European Pat. Off. .
750028  12/1996   European Pat. Off. .
9-77692  3/1997   Japan .

OTHER PUBLICATIONS

Abstract of DE 4,211,694, 1993.
Abstract of DE 4,424,647, 1995.

*Primary Examiner*—Shean C. Wu
*Attorney, Agent, or Firm*—Millen, White, Zelano & Branigan, P.C.

[57] ABSTRACT

The invention relates to bisalkenylbicyclohexanes of the formula I

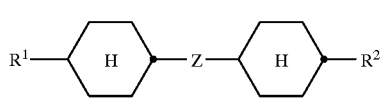

in which $R^1$, $R^2$ and Z are as defined in claim 1, and to their use in liquid-crystalline media.

11 Claims, No Drawings

BISALKENYLBICYCLOHEXANES, AND LIQUID-CRYSTALLINE MEDIUM

The invention relates to bisalkenylbicyclohexanes of the formula I,

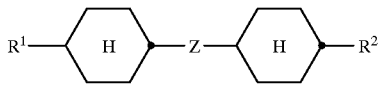

in which
$R^1$ and $R^2$ are each an alkenyl radical having 2 to 7 carbon atoms, and
Z is —CH$_2$CH$_2$—, —OCH$_2$—, —CH$_2$O—, —(CH$_2$)$_4$— or a single bond.

The invention furthermore relates to the use of these compounds as components of liquid-crystalline media, and to liquid-crystal and electro-optical display elements which contain the novel liquid-crystalline media.

The compounds of the formula I can be used as components of liquid-crystalline media, in particular for displays based on the principle of the twisted cell, the guest-host effect, the effect of deformation of aligned phases or the effect of dynamic scattering.

The invention has an object of providing novel, stable, liquid-crystalline or mesogenic compounds which are suitable as components of liquid-crystalline media and in particular simultaneously have relatively high nematogeniety.

Upon further study of the specification and appended claims, further objects and advantages of this invention will become apparent to those skilled in the art.

With regard to the very wide variety of areas of application of such compounds of low Δn and favourable viscosity values, however, it was desirable to have available further compounds of high nematogeniety which have properties precisely customized to the particular applications. The novel compounds allow the preparation of STN mixtures of surprisingly good steepness. Compared with the corresponding dialkylated compounds and monoalkenyl compounds, these substances have higher clearing points, better solubility, and a significantly lower tendency to form smectic phases.

Compounds of the formula I are covered by the broad formulae in DE-A 42 11 694, DE-A 44 146 47 and EP 0 168 683, but are not named therein. Neither the preparation of novel compounds nor the particular properties are described therein.

It has now been found that compounds of the formula I are eminently suitable as components of liquid-crystalline media. In particular, they have relatively low viscosities. They can be used to obtain stable liquid-crystalline media having a broad nematic mesophase range and advantageous optical and dielectric anisotropy values. These media furthermore have very good low-temperature behaviour.

In addition, the provision of compounds of the formula I very generally considerably broadens the range of liquid-crystalline substances which are suitable from various applicational points of view for the preparation of liquid-crystalline mixtures.

The compounds of the formula I have a broad range of application. Depending on the choice of the substituents, these compounds can be used as base materials from which liquid-crystalline media are predominantly composed. However, it is also possible to add compounds of the formula I to liquid-crystalline base materials from other classes of compound in order, for example, to modify the dielectric and/or optical anisotropy of a dielectric of this type and/or to optimize its threshold voltage and/or its viscosity.

In the pure state, the compounds of the formula I are colourless and form liquid-crystalline mesophases in a temperature range which is favourably located for electro-optical use. They are stable chemically, thermally and to light.

The invention thus relates, for example, to the compounds of the formula I and to the use of these compounds as components of liquid-crystalline media. The invention furthermore relates to liquid-crystalline media which include at least one compound of the formula I, and to liquid-crystal display elements, in particular electro-optical display elements, which contain media of this type.

Preferred compounds come under the formula IA, IB and IC:

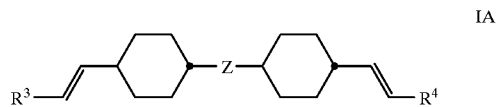

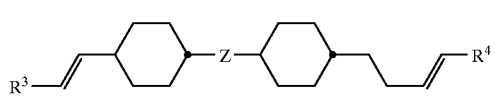

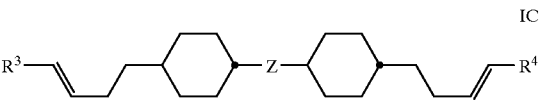

$R^3$ and $R^4$ are each, independently of one another, H or an alkyl radical having 1 to 5 carbon atoms, preferably H, CH$_3$ or C$_2$H$_5$, furthermore n-C$_3$H$_7$.

The particulary preferred subgenus of compounds are those of the subformulae I1 to I21:

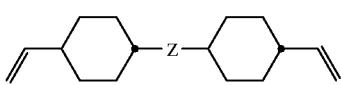

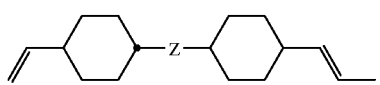

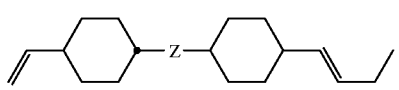

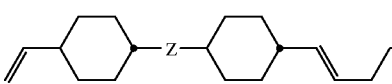

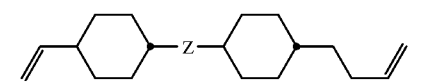

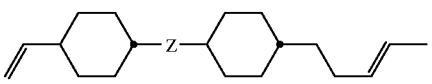

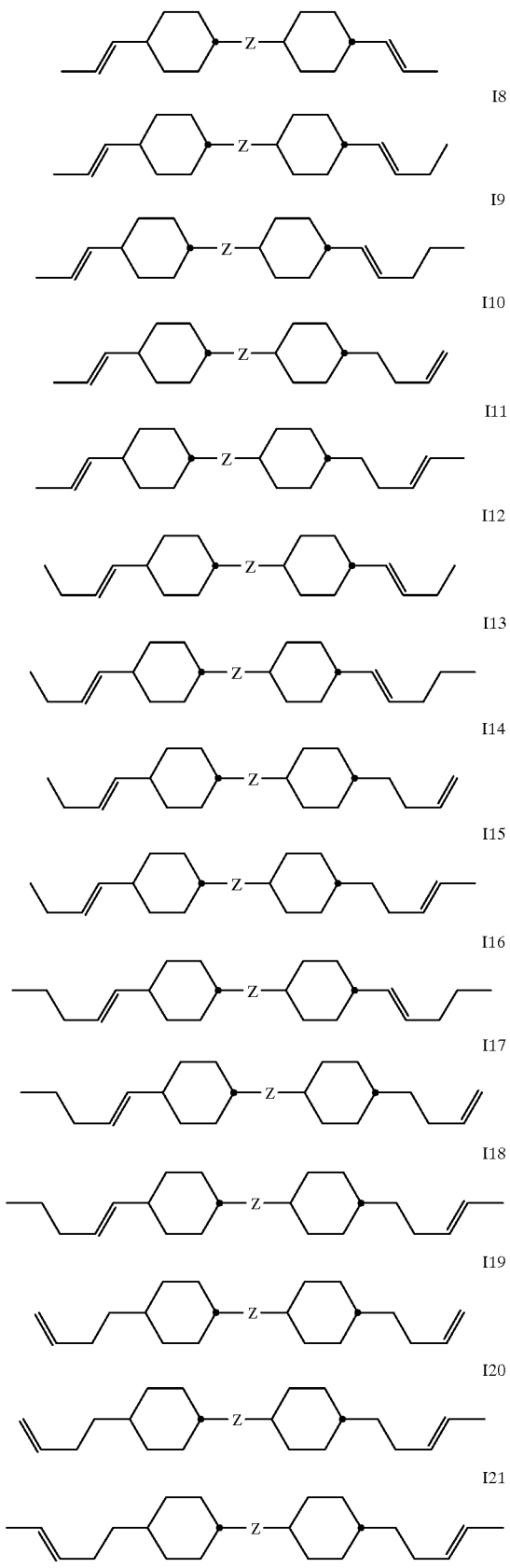

$R^1$ and $R^2$ are preferably 1E-alkenyl or 3E-alkenyl having 1–6 carbon atoms. Z is preferably a single bond or a —$CH_2CH_2$-bridge.

Compounds of the formula I which have wing groups $R^1$ and $R^2$ which are suitable for polycondensation reactions are suitable for the preparation of liquid-crystalline polycondensates.

Of these compounds of the formula I and of the subformulae, preference is given to those in which at least one of the radicals present therein has one of the preferred meanings indicated.

In the compounds of the formula I, preference is given to those stereoisomers in which the cyclohexane rings are trans-1,4-disubstituted.

The compounds of the formula I are also taken to include all compounds in which C, H and O have been replaced by the corresponding isotopes $^{13}C$, $^{14}C$, D, T, $^{17}O$ or $^{18}O$.

The compounds of the formula I are prepared by methods known per se, as described in the literature (for example in the standard works, such as Houben-Weyl, Methoden der Organischen Chemie, [Methods of Organic Chemistry], Georg-Thieme-Verlag, Stuttgart), under reaction conditions which are known and suitable for said reactions.

Use can also be made here of variants which are known per se, but are not mentioned here in greater detail.

The novel compounds can be prepared, for example, as follows:

Scheme 1

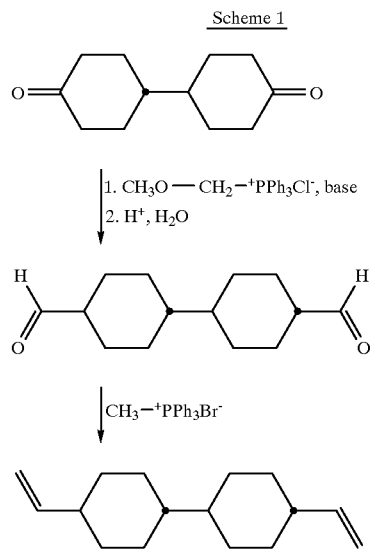

Scheme 2

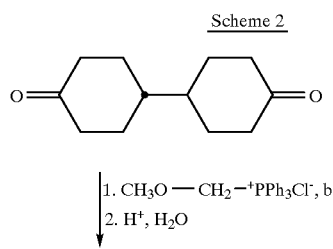

-continued
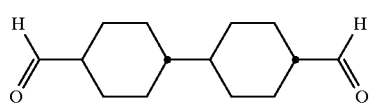
↓ alkyl—CH₂—⁺PPh₃Br⁻
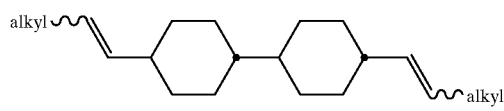
↓ isomerization
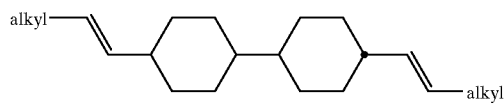
Scheme 3
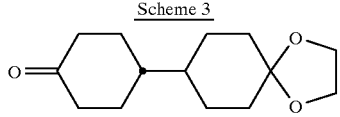
↓ 1. CH₃OCH₂—⁺PPh₃Br⁻, base
↓ 2. H⁺, H₂O
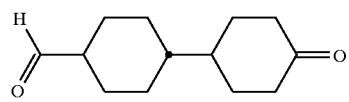
↓ CH₃—⁺PPh₃Br⁻, base
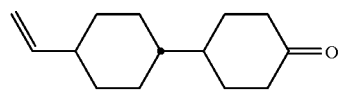
↓ 1. CH₃OCH₂—⁺PPh₃Br⁻, base
↓ 2. H⁺, H₂O
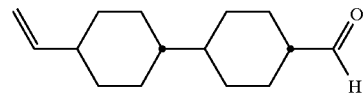
↓ alkyl—CH₂—⁺PPh₃Br⁻, base
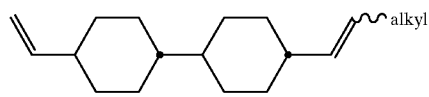
↓ isomerization
-continued
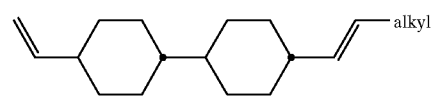
Scheme 4
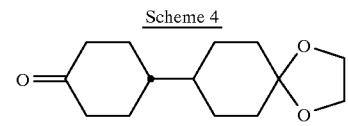
↓ 1. CH₃OCH₂—⁺PPh₃Br⁻, base
↓ 2. H⁺, H₂O
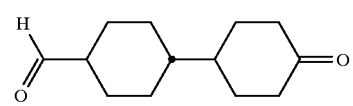
↓ alkyl—CH₂—⁺PPh₃Br⁻, base
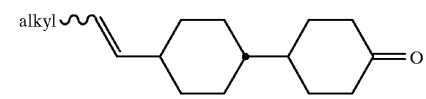
↓ 1. CH₃OCH₂—⁺PPh₃Br⁻, base
↓ 2. H⁺, H₂O
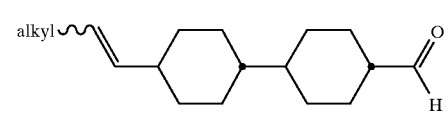
↓ alkyl'—CH₂—⁺PPh₃Br⁻, base
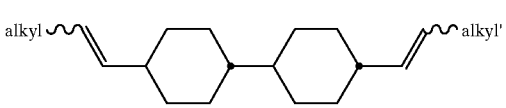
↓ isomerization
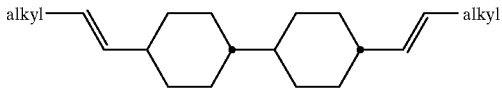

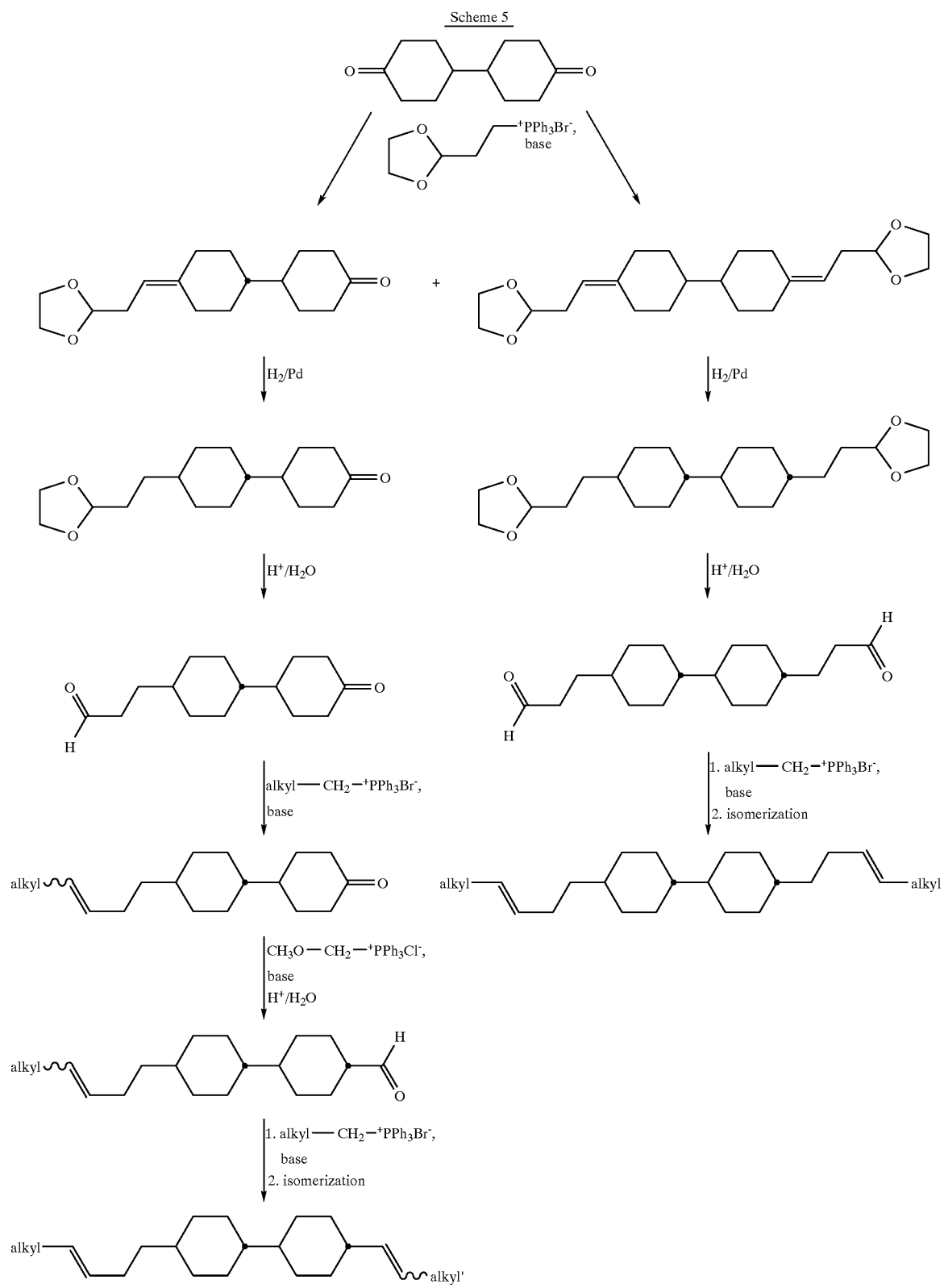

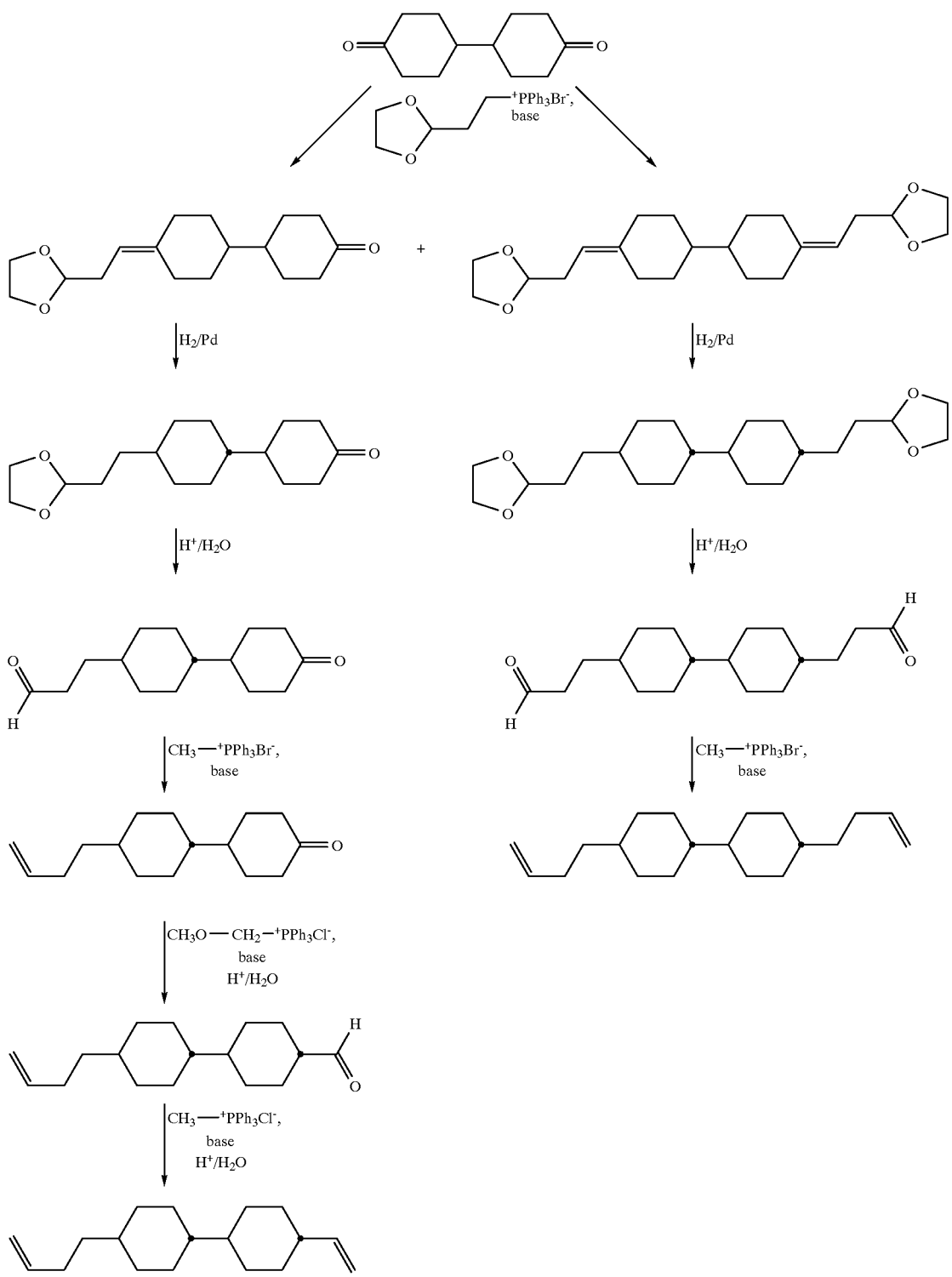

Scheme 7
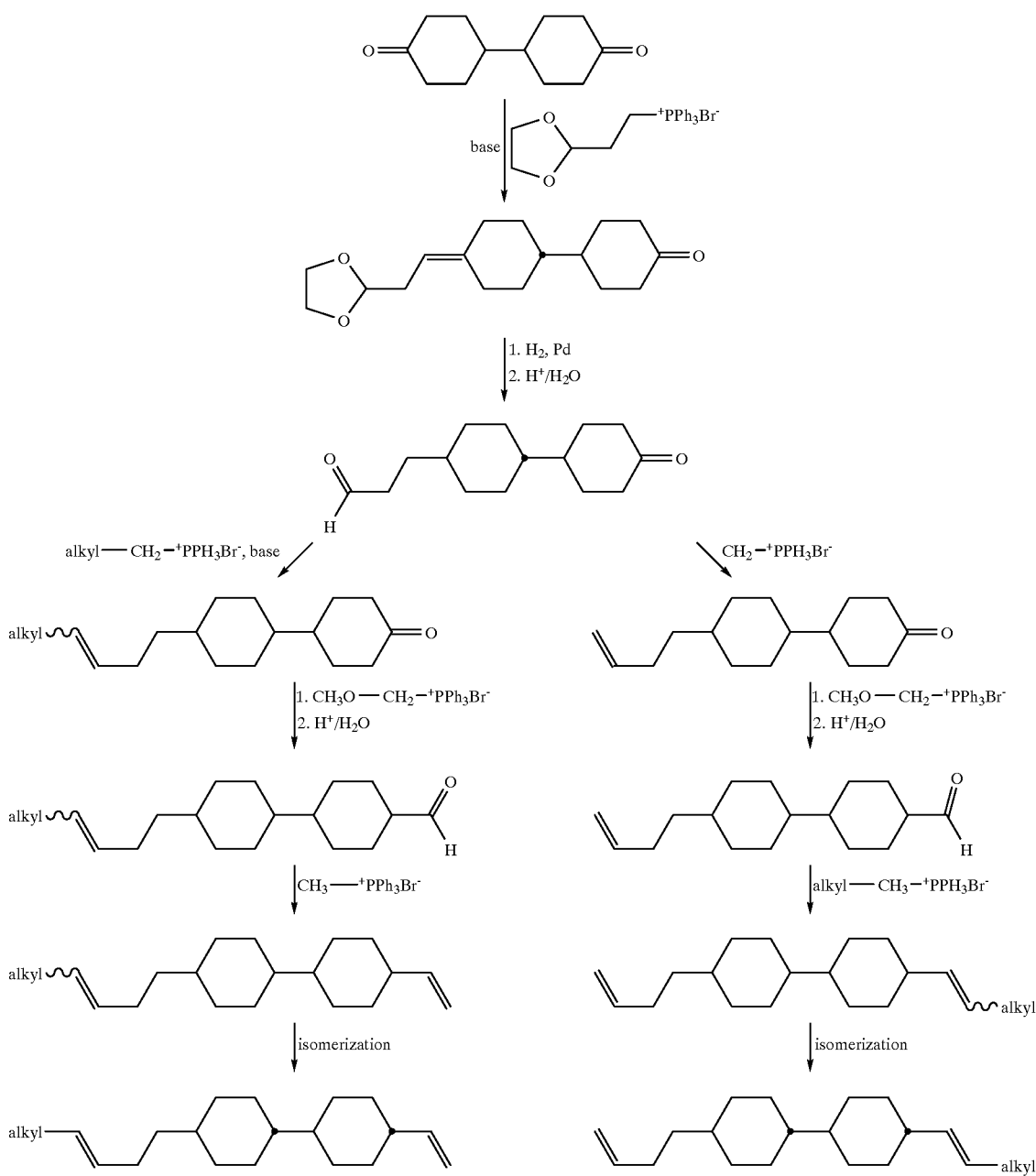
Scheme 8
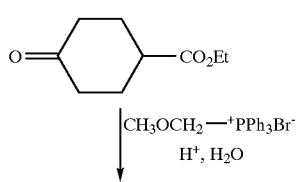
-continued
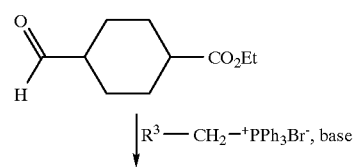

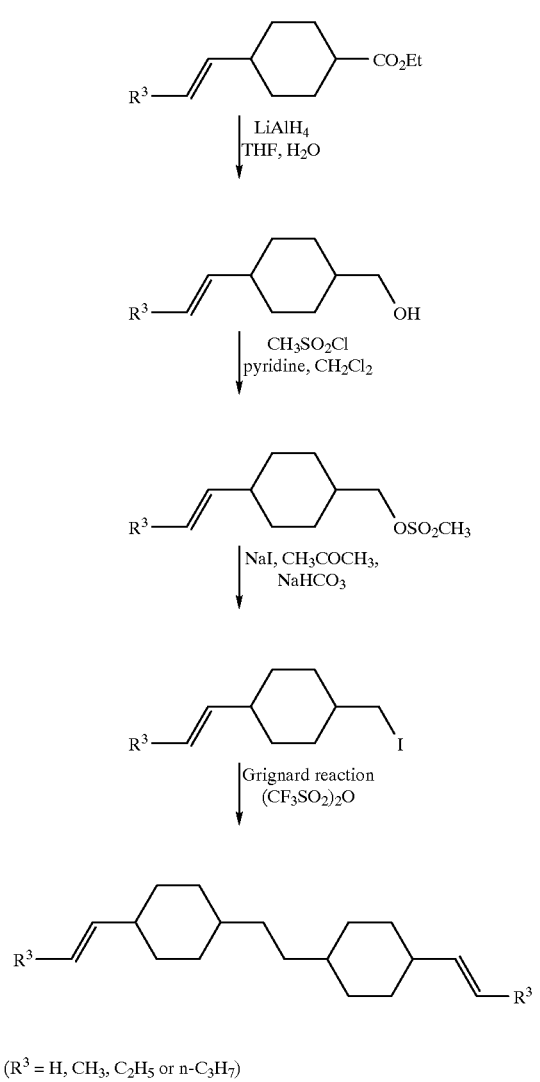

(R³ = H, CH₃, C₂H₅ or n-C₃H₇)

Scheme 9

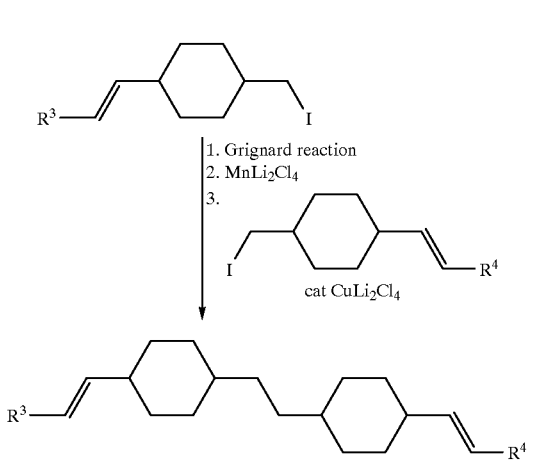

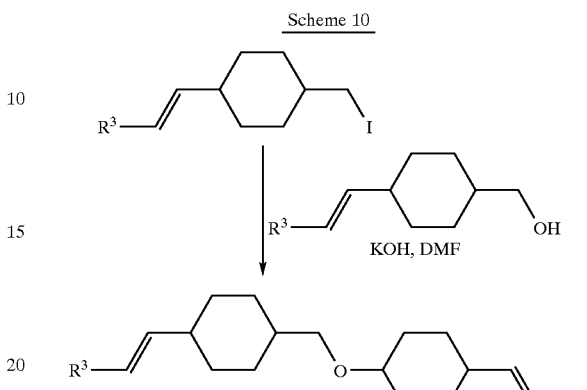

(R³ R⁴ = H, CH₃, C₂H₅, or n-C₃H₇)

Scheme 10

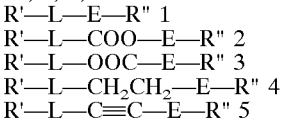

The novel liquid-crystalline media preferably comprise 2 to 40, in particular 4 to 30, components as further constituents besides one or more novel compounds. These media very particularly preferably comprise 7 to 25 components besides one or more novel compounds. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecaboxylic acid, phenylcyclohexanes, cyclohexylbiphenyls, phenylcyclohexylcyclohexanes, cyclohexylcyclohexanes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)-ethanes, 1-cyclohexyl-2-biphenylylethanes, 1-phenyl-2-cyclohexylphenylethanes optionally halogenated stilbenes, benzyl phenyl ethers, tolans and substituted cinnamic acids. The 1,4-phenylene groups in these compounds may also be fluorinated.

The most important compounds suitable as further constituents of novel media can be characterized by the formulae 1, 2, 3, 4 and 5:

R'—L—E—R"   1
R'—L—COO—E—R"   2
R'—L—OOC—E—R"   3
R'—L—CH₂CH₂—E—R"   4
R'—L—C≡C—E—R"   5

In the formulae 1, 2, 3, 4 and 5, L and E, which may be identical or different, are in each case, independently of one another, a bivalent radical from the group formed by —Phe—, —Cyc—, —Phe—Phe—, —Phe—Cyc—, —Cyc—Cyc—, —Pyr—, —Dio—, —G—Phe— and —G—Cyc— and their mirror images, where Phe is unsubstituted or fluorine-substituted 1,4-phenylene, Cyc is trans-1,4-cyclohexylene or 1,4-cyclohexylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe—Cyc. The novel media preferably comprise one or more components selected from the compounds of the formulae 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of Cyc, Phe and Pyr and the other radical is selected from the group consisting of —Phe—Phe—, —Phe—Cyc—, —Cyc—Cyc—, —G—Phe— and —G—Cyc—, and optionally one or more components selected from the compounds of the formulae 1, 2, 3, 4 and 5 in which the radicals L and E are selected from the group consisting of —Phe—Cyc—, —Cyc—Cyc—, —G—Phe— and —G—Cyc—.

In a smaller sub-group of the compounds of the formulae 1, 2, 3, 4 and 5, R' and R" are in each case, independently of one another, alkyl, alkenyl, alkoxy, alkoxyalkyl, alkenyloxy or alkanoyloxy having up to 8 carbon atoms. This smaller sub-group is called group A below, and the compounds are labeled with the subformulae 1a, 2a, 3a, 4a and 5a. In most of these compounds, R' and R" are different from one another, one of these radicals usually being alkyl, alkenyl, alkoxy or alkoxyalkyl.

In another smaller sub-group of the compounds of the formulae 1, 2, 3, 4 and 5 which is known as group B. R" is —F, —Cl, —NCS or —(O)$_i$CH$_{3-(k+l)}$F$_k$Cl$_l$, where i is 0 or 1, and k+l is 1, 2 or 3; the compounds in which R" has this meaning are labeled with the sub-formulae 1b, 2b, 3b, 4b and 5b. Particular preference is given to those compounds of the sub-formulae 1b, 2b, 3b, 4b and 5b in which R" is —F, —Cl, —NCS, —CF$_3$, —OCHF$_2$ or —OCF$_3$.

In the compounds of the sub-formulae 1b, 2b, 3b, 4b and 5b, R' is as defined for the compounds of the sub-formulae 1a–5a and is preferably alkyl, alkenyl, alkoxy or alkoxyalkyl.

In a further smaller sub-group of the compounds of the formulae 1, 2, 3, 4 and 5, R" is —CN; this sub-group is known as group C below, and the compounds of this sub-group are correspondingly described by sub-formulae 1c, 2c, 3c, 4c and 5c. In the compounds of the sub-formulae 1c, 2c, 3c, 4c and 5c, R' is as defined for the compounds of the sub-formulae 1a-5a and is preferably alkyl, alkoxy or alkenyl.

In addition to the preferred compounds of groups A, B and C, other compounds of the formulae 1, 2, 3, 4 and 5 having other variants of the proposed substituents are also customary. All these substances can be obtained by methods which are known from the literature or analogously thereto.

Besides novel compounds of the formula I, the novel media preferably comprise one or more compounds selected from group A and/or group B and/or group C. The proportions by weight of the compounds from these groups in the novel media are preferably Group A: 0 to 90%, preferably 20 to 90%, in particular 30 to 90%

Group B: 0 to 80%, preferably 10 to 80%, in particular 10 to 65%

Group C: 0 to 80%, preferably 5 to 80%, in particular 5 to 50%, the sum of the proportions by weight of the group A and/or B and/or C compounds present in the particular novel media preferably being 5%–90%, and in particular, 10% to 90%.

The novel media preferably comprise 1 to 40%, particularly preferably 5 to 30%, of one or more compounds of formula I. Further preferred media are those which comprise more than 40%, in particular 45 to 90%, of one or more compounds of formula I. The media preferably comprise three, four or five compounds of formula I.

The novel media are prepared in a manner which is customary per se. In general, the components are dissolved in one another, expediently at elevated temperature. By means of suitable additives, the liquid crystalline phases can be modified in accordance with the invention in a manner such that they can be used in all types of liquid-crystal display elements which have hitherto been disclosed. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of colored guest-host systems, or substances can be added to modify the dielectric anisotropy, the viscosity and/or the orientation of the nematic phases.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German applications No. 196 40 851.2, filed Oct. 2, 1996, and 197 07 950.4, filed Feb. 27, 1997, are hereby incorporated by reference.

EXAMPLES

In the present application and in the examples below, the structures of the liquid-crystal compounds are indicated by acronyms, the transformation into chemical formulae taking place as in Tables A and B below. All the radicals C$_n$H$_{2n+1}$ and C$_m$H$_{2m+1}$ are straight-chain alkyl radicals containing n or m carbon atoms respectively (n and m=1–15). The coding in Table B is self-evident. In Table A, only the acronym for the parent structure is given. In individual cases, the acronym for the parent structure is followed, separated by a hyphen, by a code for the substituents R$^1$, R$^2$, L$^1$ and L$^2$:

| Code for R$^1$, R$^2$, L$^1$ and L$^2$ | R$^1$ | R$^2$ | L$^1$ | L$^2$ |
|---|---|---|---|---|
| nm | C$_n$H$_{2n+1}$ | C$_m$H$_{2m+1}$ | H | H |
| nOm | C$_n$H$_{2n+1}$ | OC$_m$H$_{2m+1}$ | H | H |
| nO.m | OC$_n$H$_{2n+1}$ | C$_m$H$_{2m+1}$ | H | H |
| n | C$_n$H$_{2n+1}$ | CN | H | H |
| nN.F | C$_n$H$_{2n+1}$ | CN | H | F |
| nF | C$_n$H$_{2n+1}$ | F | H | H |
| nOF | OC$_n$H$_{2n+1}$ | F | H | H |
| nCl | C$_n$H$_{2n+1}$ | Cl | H | H |
| nF.F | C$_n$H$_{2n+1}$ | F | H | F |
| nF.F F | C$_n$H$_{2n+1}$ | F | F | F |
| nCF$_3$ | C$_n$H$_{2n+1}$ | CF$_3$ | H | H |
| nOCF$_3$ | C$_n$H$_{2n+1}$ | OCF$_3$ | H | H |
| nOCF$_2$ | C$_n$H$_{2n+1}$ | OCHF$_2$ | H | H |
| nS | C$_n$H$_{2n+1}$ | NCS | H | H |
| rVsN | CrH$_{2r+1}$—CH=CH—C$_s$H$_{2s}$— | CN | H | H |
| rEsN | CrH$_{2r+1}$—O—C$_s$H$_{2s}$— | CN | H | H |
| nAm | C$_n$H$_{2n+1}$ | COOC$_m$H$_{2m+1}$ | H | H |
| nOCCF$_2$.F.F | C$_n$H$_{2n+1}$ | OCH$_2$CF$_2$H | F | F |

TABLE A
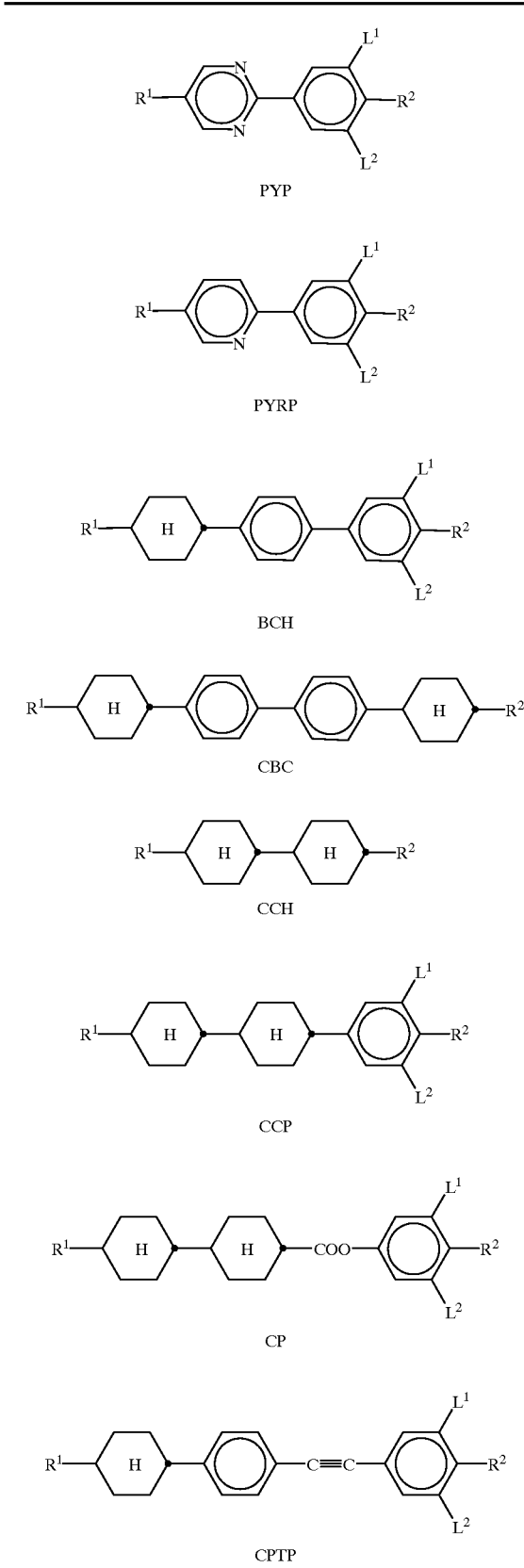
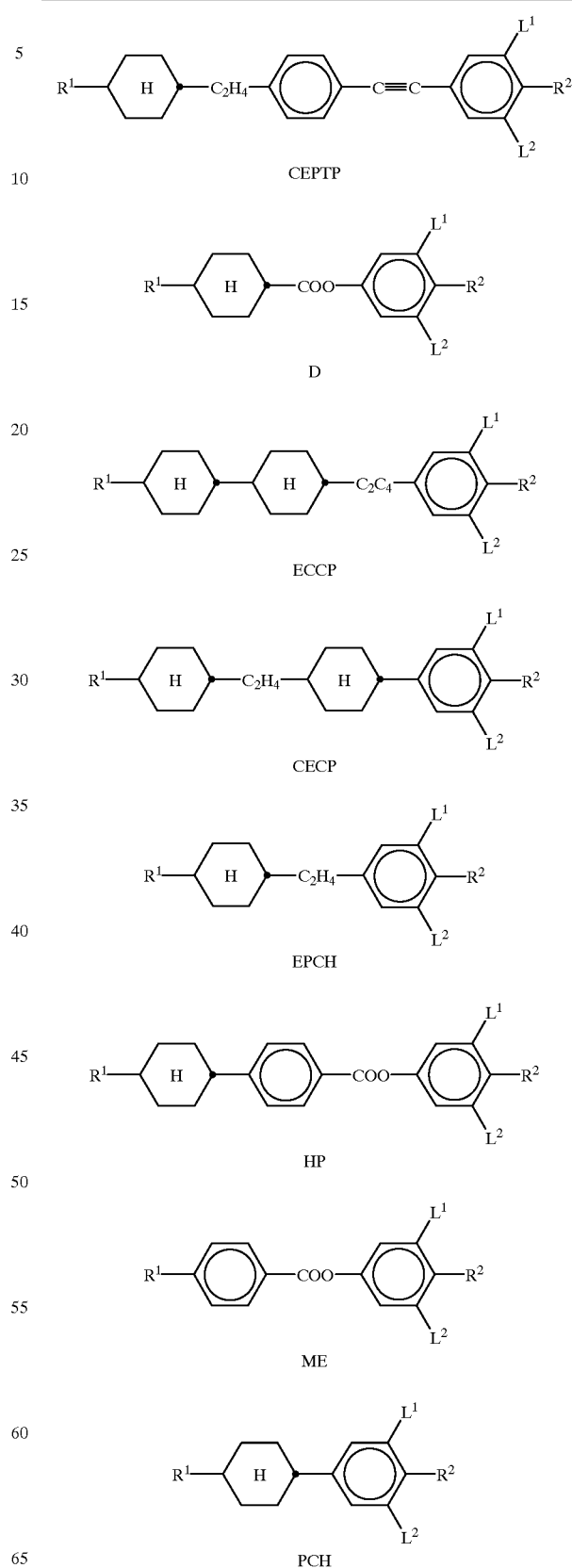

TABLE A-continued

PDX

PTP

BECH

EBCH

CPC

B

TABLE B

T15

K3n

M3n

BCH-n.Fm

TABLE B-continued

Inm

C-nm

CBC-nmF

CCPC-nm

CH-nm

HD-nm

HH-nm

OS-nm

CHE

ECCH-nm

CC-V-V

CC-1V-V1

CC-2V-V2

CC-V2-2V

TABLE B-continued

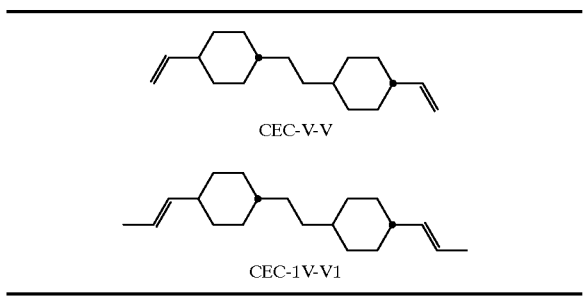

CEC-V-V

CEC-1V-V1

The examples below are intended to illustrate the invention without representing a limitation. Above and below, percent data are percent by weight. All temperatures are given in degrees Celsius. mp.=melting point, cp.=clearing point. Furthermore, C=crystalline state, N=nematic phase, S=smectic phase and I=isotropic phase. The number between two symbols indicates the conversion temperature in degrees Celsius. Δn denotes optical anisotropy (589 nm, 20° C.), and the viscosity (mm²/sec) was determined at 20° C.

"Conventional work-up" means that water is added if necessary, the mixture is extracted with dichloromethane, diethyl ether, methyl tert-butyl ether or toluene, the organic phase is separated off, dried and evaporated, and the product is purified by distillation under reduced pressure or crystallization and/or chromatography. The following abbreviations are used:

| | |
|---|---|
| DMF | N,N-dimethylformamide |
| DMEU | 1,3-dimethyl-2-imidazolidinone |
| POT | potassium tertiary-butoxide |
| THF | tetrahydrofuran |
| pTsOH | p-toluenesulfonic acid |

Example 1

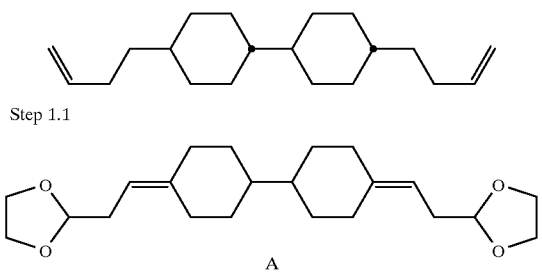

Step 1.1

A 1.55 mol of 2-(1,3-dioxolan-2-ylethyl) triphenylphosphonium bromide are suspended in 800 ml of absolute THF at 0–5° C., and 1.55 mol of potassium tert-butoxide dissolved in 500 ml of absolute THF are added under N₂. 150 g of bicyclohexane-1,4-dione dissolved in 200 ml of absolute THF are then added to the suspension at 0–5° C. The mixture is allowed to warm to room temperature, and is then stirred overnight, hydrolysed and finally subjected to customary work-up.

Step 1.2

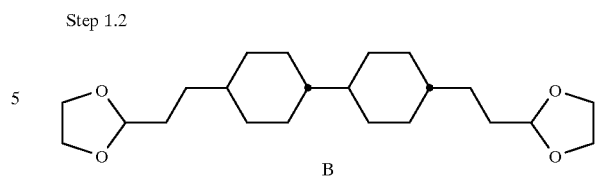

B 0.3 mol of A are hydrogenated in 1000 ml of absolute THF in the presence of Pd/C (5%). When hydrogenation is complete, the mixture is filtered, the filtrate is evaporated, and the residue is crystallized from ethanol.

Step 1.3

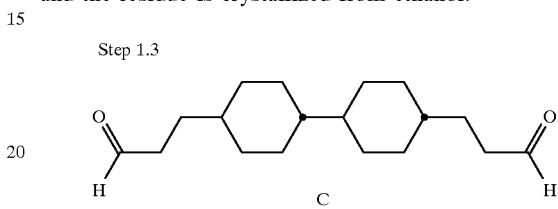

C 0.085 mol of B are dissolved in 600 ml of toluene, and 250 ml of formic acid are added with stirring at room temperature. The two-phase mixture is stirred overnight under an inert-gas atmosphere. After addition of water and toluene, the mixture is subjected to conventional work-up.

Step 1.4

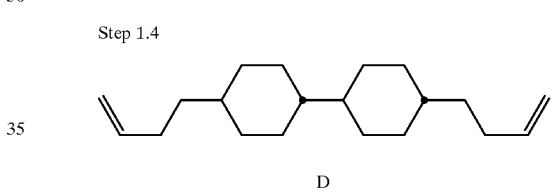

D 0.025 mol of C and 0.052 mol of methyltriphenylphosphonium bromide are dissolved in 70 ml of absolute THF and introduced into a flask at 0° C. under an argon atmosphere, and 0.052 mol of potassium tert-butoxide dissolved in 80 ml of THF are added in portions at −70° C. The mixture is stirred overnight at room temperature. Water and 2N hydrochloric acid are added, and the mixture is subjected to conventional work-up. The product is recrystallized from 2-propanol. C 2 $S_B$ 58 N 77.6 I; Δn=+0.052; Δε=−0.87; $v_{20}$=6

The following compounds of the formula

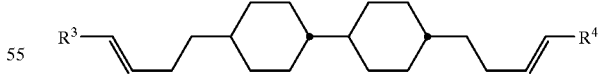

are prepared analogously:

| $R^3$ | $R^4$ |
|---|---|
| $CH_3$ | $CH_3$ |
| $C_2H_5$ | $C_2H_5$ |
| $n-C_3H_7$ | $n-C_3H_7$ |

Example 2

Step 2.1

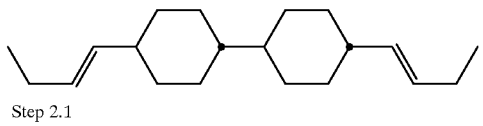

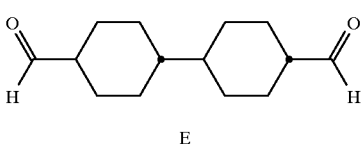

E 0.30 ml of bicyclohexane-1,4-dione and 0.7 mol of methoxymethyltriphenylphosphonium chloride are suspended in 1000 ml of tert-butyl methyl ether. The mixture is cooled to 0–5° C., and 0.7 mol of potassium tert-butoxide dissolved in 500 ml of absolute THF is added in portions. The reaction solution is stirred at room temperature for 5 days. 10% HCl is added, and the mixture is stirred at 50° C. for a further 3 hours. Water and tert-butyl methyl ether are added, and the mixture is finally subjected to conventional work-up.

Step 2.2

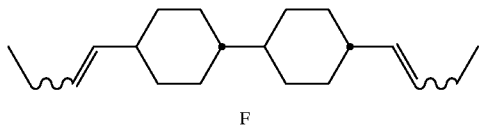

F

Potassium tert-butoxide is added in portions to 0.41 mol of E and 0.82 mol of propyltriphenylphosphonium bromide in 1000 ml of absolute THF. The reaction mixture is stirred overnight at room temperature. Water, 2N HCl and tert-butyl methyl ether are added, and the mixture is subjected to conventional work-up.

Step 2.3

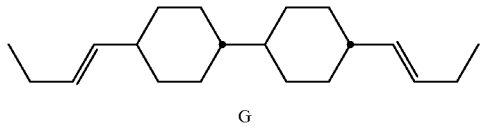

G 0.049 mol of F, 80 ml of toluene, 2 g of sodium benzenesulfonate and 16 ml of 1N HCl are refluxed for 2 days. Water is added, and the mixture is subjected to conventional work-up. The product is recrystallized from 2-propanol. C 25 $S_B$ 86 N 87 I; $\Delta n$=+0.063; $\Delta\epsilon$=−0.62.

The following compounds of the formula

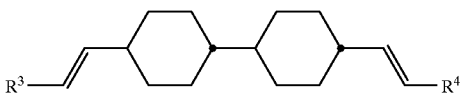

are prepared analogously:

| $R^3$ | $R^4$ | |
|---|---|---|
| H | H | C −9 N 20.4 I; $\Delta n$ = +0.035; $\Delta\epsilon$ = −1.93 |
| $CH_3$ | $CH_3$ | C 33 $S_B$ 70 N 109.9 I; $\Delta n$ = +0.081; $\Delta\epsilon$ = −0.02 |
| $C_2H_5$ | $C_2H_5$ | |
| $n-C_3H_7$ | $n-C_3H_7$ | |

Example 3

Step 3.1

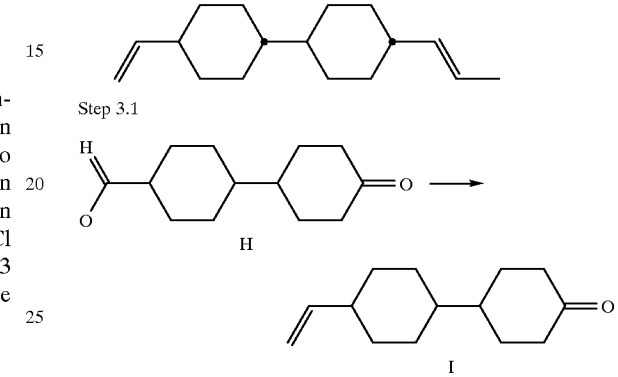

0.7 mol of potassium tert-butoxide dissolved in 500 ml of absolute THF is added dropwise at room temperature to 0.7 mol of methyltriphenylphosphonium bromide in 1400 ml of absolute THF. The suspension is stirred for 0.5 hour, and 0.68 mol of H dissolved in 900 ml of absolute THF is then added. The mixture is stirred for 4 hours, water is added, the mixture is extracted with methyl tert-butyl ether, and the extract is then subjected to conventional work-up.

Step 3.2

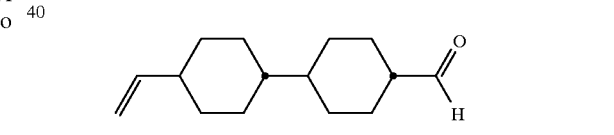

J 0.5 mol of I and 0.6 mol of methoxytriphenylphosphonium chloride are dissolved in 1000 ml of absolute THF, and a solution of 0.6 mol of potassium tert-butoxide in 200 ml of absolute THF is added at about 10° C. The suspension is stirred overnight, water and methyl tert-butyl ether are added, and the mixture is subjected to conventional work-up.

Step 3.3

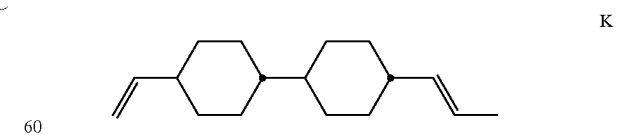

K 0.1 mol of J and 0.1 mol of ethyltriphenylphosphonium bromide are dissolved in 200 ml of absolute THF, and 0.1 mol of potassium tert-butoxide is added in portions at room temperature. The reaction mixture is stirred overnight, water is added, and the mixture is neutralized using dilute HCl and subjected to conventional work-up.

For cis/trans isomerization, the product (0.04 mol) is dissolved in 80 ml of toluene, 3.7 g of sodium benzenesulfinate and 23 ml of 1N HCl are added, and the mixture is refluxed overnight. The reaction solution is allowed to cool to room temperature, bicarbonate solution is added, and the mixture is finally subjected to conventional work-up. C-16 N 54.3 I; Δε=−0.92; Δn=+0.060.

The following compounds of the formula

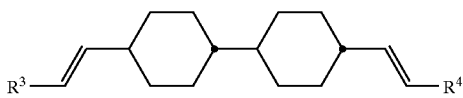

are prepared analogously:

| $R^3$ | $R^4$ | |
|---|---|---|
| H | $CH_3$ | |
| H | $C_2H_5$ | C −28 $S_B$ 30 N 39.1 I; Δn = +0.049; Δε = −1.12 |
| H | n-$C_3H_7$ | C −32 $S_B$ 49 N 54.8 I; Δn = +0.056; Δε = −0.99 |
| $CH_3$ | $C_2H_5$ | C 13 $S_B$ 29 N 78.9 I; Δn = +0.065; Δε = −0.6 |
| $CH_3$ | n-$C_3H_7$ | C 7 $S_B$ 62 N 100.8 I; Δn = +0.074; Δε = −0.2 |
| $C_2H_5$ | n-$C_3H_7$ | |

Example 4

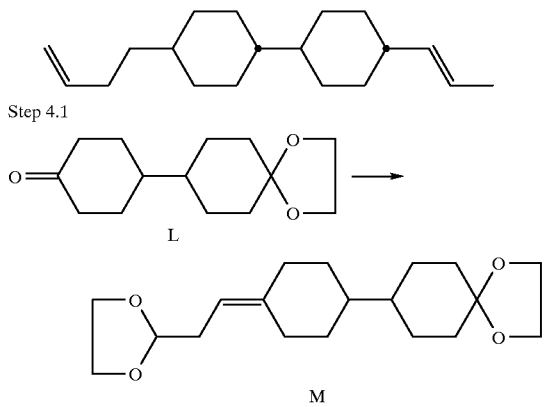

1.15 mol of potassium tert-butoxide dissolved in 400 ml of absolute THF are added dropwise at about 10° C. to 1.15 mol of dioxolanethyltriphenylphosphonium bromide in 1.8 l of absolute THF. The suspension is stirred for 15 minutes, and 1.05 mol of L dissolved in 700 ml of absolute THF are added at 10° C. The reaction mixture is stirred overnight, water is added, and the mixture is neutralized using dilute HCl. After extraction with methyl tert-butyl ether, the extract is subjected to conventional work-up.

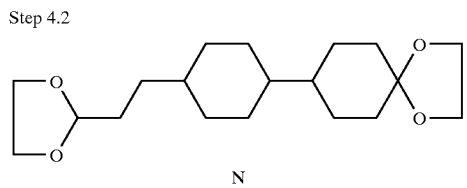

0.65 mol of M dissolved in 2.5 l of THF is hydrogenated in the presence of 30 g of Pd/C. When the reaction is complete, the catalyst is filtered off, and the filtrate is evaporated in a rotary evaporator.

Step 4.3

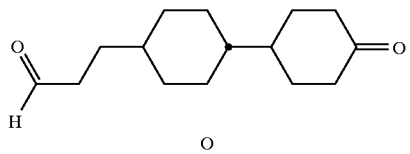

0.7 mol of N, 1000 ml of formic acid and 3000 ml of toluene are stirred overnight at room temperature. Water is added to the reaction solution, and the mixture is subjected to conventional work-up.

Step 4.4

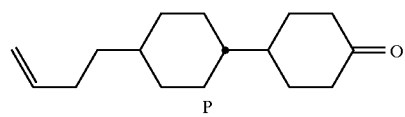

A solution of 0.5 mol of potassium tert-butoxide in 300 ml of absolute THF is added dropwise at room temperature to 0.5 mol of methyltriphenylphosphonium bromide in 1200 ml of absolute THF. The reaction mixture is stirred for 0.5 hour, and 0.5 mol of O dissolved in 500 ml of absolute THF is then added. The reaction mixture is stirred at room temperature for 4 hours, diluted with water and extracted with methyl tert-butyl ether, and the extract is subjected to conventional work-up.

Step 4.5

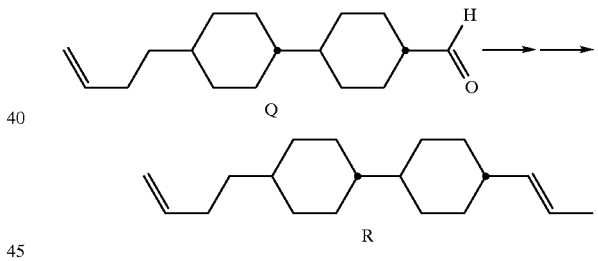

Analogously to step 3.2 and step 3.3, 0.09 mol of P is converted firstly into the aldehyde O and then into the bisalkenyl compound R, which is, finally, subjected to cis/trans isomerization. C 4 $S_B$ 17 N 84 I; Δn=+0.066; Δε=0.38

The following compounds of the formula

are prepared analogously:

| $R^3$ | $R^4$ | |
|---|---|---|
| H | H | C −48 $S_B$ 1 N 49 I; Δn = +0.045; Δε = −1.14; $v_{20}$ = 4 |

-continued

| R$^3$ | R$^4$ | |
|---|---|---|
| H | C$_2$H$_4$ | C -4 S$_B$ 77 N 78.8 I; Δn = +0.061; Δε = -0.66 |
| H | n-C$_3$H$_7$ | |
| C$_2$H$_5$ | H | |
| C$_2$H$_5$ | CH$_3$ | |
| C$_2$H$_5$ | C$_2$H$_5$ | |
| C$_2$H$_5$ | n-C$_3$H$_7$ | |
| n-C$_3$H$_7$ | H | |
| n-C$_3$H$_7$ | CH$_3$ | |
| n-C$_3$H$_7$ | C$_2$H$_5$ | |
| n-C$_3$H$_7$ | n-C$_3$H$_7$ | |

Example 5

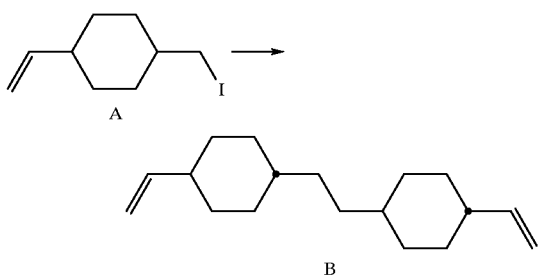

Analogously to steps 4.1, 4.2, 4.3 and 4.4 P is reacted with dioxolanmethyltriphenylphosphonium bromide, the product is hydrogerated, converted firstly into the aldehyde, and then to the bisalkanyl compound S, which is finally subjected to cis/trans isomerization.

C 29 S$_B$ 57 I; Δε=-1.8; Δn=+0.027

Example 6

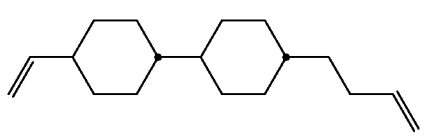

One drop of methyl iodide is added to a mixture of 37 mmol of A (prepared as in Scheme 8) in 100 ml of diethyl ether and 38.5 mmol of magnesium. When the Grignard reaction is complete, the reaction mixture is allowed to cool to room temperature, and 7 mmol of trifluoromethane-sulfonic anhydride dissolved in 20 ml of diethyl ether are added in portions.

The reaction mixture is stirred at the boil for 0.5 hour, hydrolysed and subjected to conventional work-up. The crude product is eluted on silica gel using N-hexane and finally recrystallized from hexane/ethanol (1:5).

C 25 N 25.7 I; Δn=+0.031; Δε=-2.12; ν$_{20}$=5

The following compounds of the formula

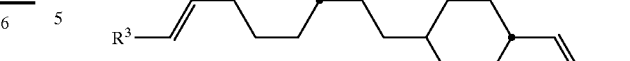

are prepared analogously:

| R$^3$ | R$^4$ | |
|---|---|---|
| CH$_3$ | CH$_3$ | C -1 S 88 N 88.9 I; Δn = 0.071; Δε = 0.16 |
| C$_2$H$_5$ | C$_2$H$_5$ | |
| n-C$_3$H$_7$ | n-C$_3$H$_7$ | |

Example 7

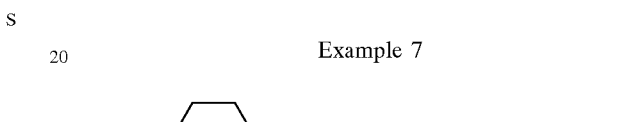

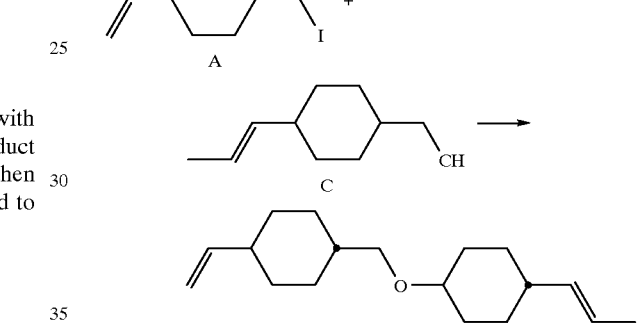

0.1 mol of A is converted into the Grignard compound analogously to Example 6, and this solution is added drop-wise at -10° C. to a solution of 0.1 mol of MnLi$_2$Cl$_4$ in THF (prepared from MnCl$_2$ and LiCl). 0.1 mol of C and 0.002 mol of CuLi$_2$Cl$_4$ (dissolved in THF) are then added, and the mixture is stirred at room temperature for 3 hours. Finally, the mixture is subjected to conventional work-up.

The following compounds of the formulae

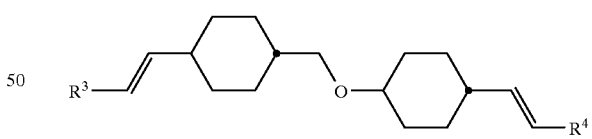

are prepared analogously:

| R$^3$ | R$^4$ |
|---|---|
| H | H |
| H | C$_2$H$_5$ |
| H | n-C$_3$H$_7$ |
| CH$_3$ | C$_2$H$_5$ |
| CH$_3$ | n-C$_3$H$_7$ |
| C$_2$H$_5$ | C$_2$H$_5$ |
| C$_2$H$_5$ | n-C$_3$H$_7$ |
| n-C$_3$H$_7$ | n-C$_3$H$_7$ |

Comparative Example 1

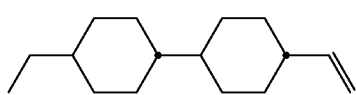

C-41 $S_B$ 29 I
$v_{20}[mm^2 \times s^{-1}]$: 5

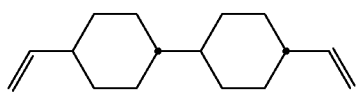

C-9 N 20.4 I
$v_{20}[mm^2 \times s^{-1}]$: 5

Comparative Example 2

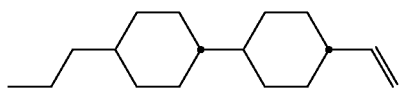

C-23 $S_B$ 33 N 49 I

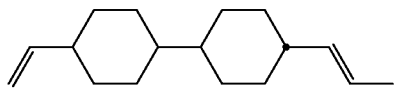

C-16 N 55 I

Comparative Example 3

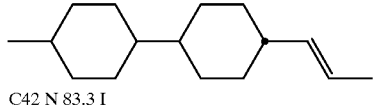

C42 N 83.3 I
$v_{20}[mm^2 \times s^{-1}]$: 9

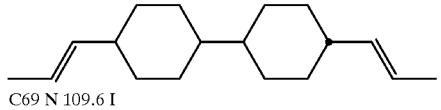

C69 N 109.6 I
$v_{20}[mm^2 \times s^{-1}]$: 6

Comparative Example 4

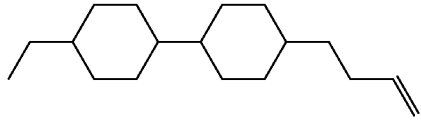

C-36 $S_B$ 55 I

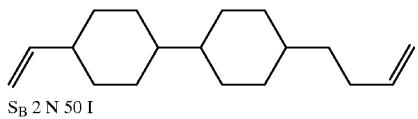

$S_B$ 2 N 50 I

Comparative Example 5

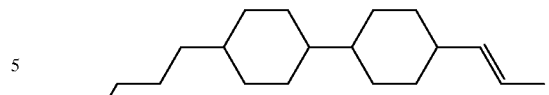

C1 $S_B$ 67 N 82.3 I

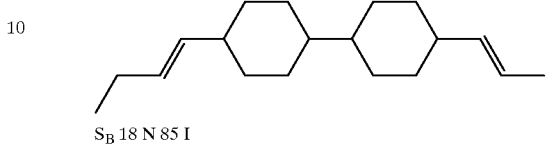

$S_B$ 18 N 85 I

Comparative Examples 1–5 show that the novel dialkenyl compounds have a lower tendency to form smectic phases, a higher clearing point and lower viscosity than the corresponding monoalkenyl compounds.

What is claimed is:

1. A bisalkenylbicyclohexane compound of the formula I

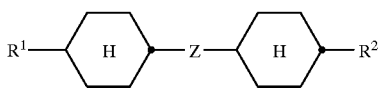

in which $R^1$ and $R^2$ are independently each an alkenyl radical having 2 to 7 carbon atoms, and Z is —$CH_2CH_2$—, —$OCH_2$—, —$CH_2O$—, or a single bond.

2. A compound according to claim 1, wherein $R^1$ and $R^2$ are each, independently of one another, 1E-alkenyl or 3E-alkenyl.

3. A compound according to claim 1, wherein Z is —$CH_2CH_2$— or a single bond.

4. A compound according to claim 1, of the formula IA:

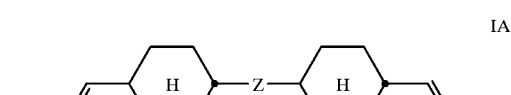

in which $R^3$ and $R^4$ are each, independently of one another, H or an alkyl radical having 1 to 5 carbon atoms.

5. A compound according to claim 1, of the formula IB:

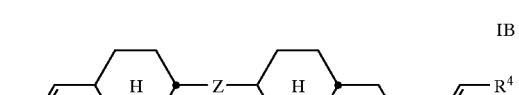

in which $R^3$ and $R^4$ are each, independently of one another, H or an alkyl radical having 1 to 5 carbon atoms.

6. A compound according to claim 1, of the formula IC:

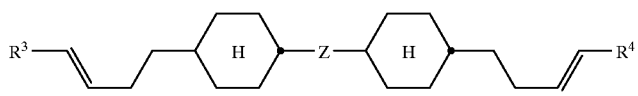

R³ and R⁴ are each, independently of one another, H or an alkyl radical having 1 to 5 carbon atoms.

7. A compound according to claim 1 of the formula:

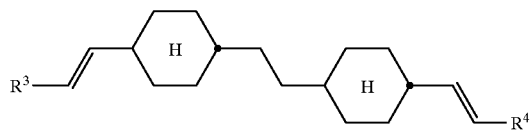

in which

R³ and R⁴ are each, independently of one another, H or an alkyl radical having 1 to 5 carbon atoms.

8. A compound according to claim 1 of the following formula:

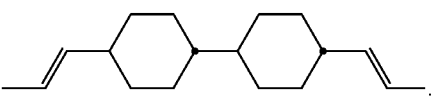

9. A liquid-crystalline medium having at least two liquid-crystalline components, wherein at least one of the liquid-crystalline components is a compound of claim 1.

10. A liquid-crystal display element, which comprises a liquid-crystalline medium according to claim 9.

11. An electro-optical display element, which comprises, as dielectric, a liquid-crystalline medium according to claim 9.

* * * * *